United States Patent [19]

Bruderer et al.

[11] Patent Number: 4,559,403
[45] Date of Patent: Dec. 17, 1985

[54] SUBSTITUTED ISOQUINOLINES

[75] Inventors: Hans Bruderer, Biel-Benken, Switzerland; Richard W. Kierstead, North Caldwell; John G. Mullin, Jr., Hawthorne, both of N.J.; Keiji Nakamura, Kamakura; Mitsuru Tateishi, Atsugi, both of Japan; Sidney Teitel, Clifton; Jay P. O'Brien, Cedar Grove, both of N.J.

[73] Assignee: Hoffmann-La Roche Inc., Nutley, N.J.

[21] Appl. No.: 705,262

[22] Filed: Feb. 25, 1985

Related U.S. Application Data

[62] Division of Ser. No. 496,327, May 19, 1983, abandoned.

[51] Int. Cl.[4] ............................................ C07D 217/16
[52] U.S. Cl. .................................... 546/144; 544/363; 546/147; 546/149
[58] Field of Search ........................ 546/144, 147, 149

[56] References Cited

U.S. PATENT DOCUMENTS

| 4,003,903 | 1/1977 | Schwartz | 546/147 |
| 4,055,648 | 10/1977 | Sache | 546/149 |
| 4,491,665 | 1/1985 | El-Sayad et al. | 546/147 |
| 4,501,891 | 2/1985 | Buzas et al. | 546/149 |

Primary Examiner—Glennon H. Hollrah
Assistant Examiner—James H. Turnipseed
Attorney, Agent, or Firm—Jon S. Saxe; Bernard S. Leon; William G. Isgro

[57] ABSTRACT

Substituted isoquinolines of the formula

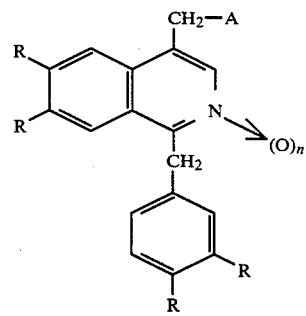

wherein
R is a lower alkoxy, n is the integer zero or 1, and A is

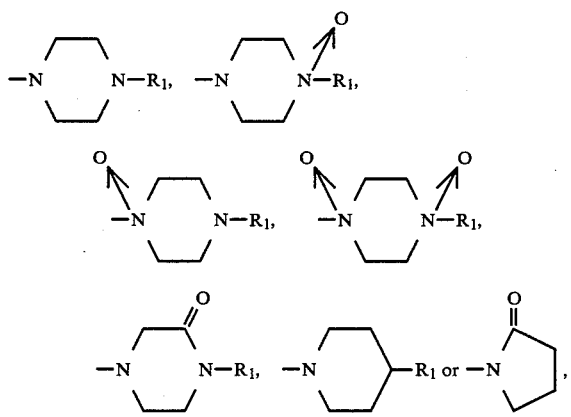

wherein $R_1$ is phenyl halophenyl, lower-alkylphenyl or lower-alkoxyphenyl, and pharmaceutically acceptable acid addition salts thereof, are described. The compounds of formula I are useful in the treatment of cerebral and cardiac ischemias.

8 Claims, No Drawings

SUBSTITUTED ISOQUINOLINES

This is a division, of application Ser. No. 496,327 filed May 19, 1983, now abandoned.

BRIEF SUMMARY OF THE INVENTION

The invention relates to substituted isoquinolines of the formula

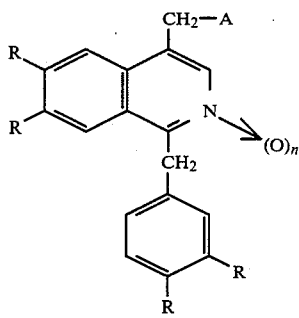

wherein
R is lower alkoxy, n is the integer zero or 1, and A is

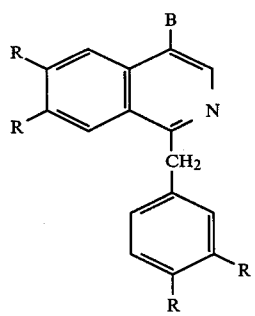

wherein $R_1$ is phenyl, halophenyl, lower-alkylphenyl or lower-alkoxyphenyl, and pharmaceutically acceptable acid addition salts thereof.

In another aspect, the invention relates to intermediates of the formula

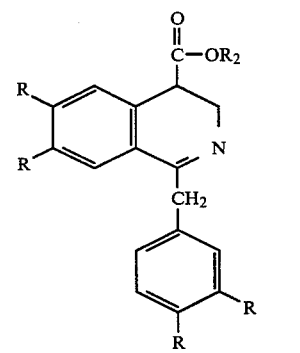

wherein R is lower alkoxy, and B is hydroxymethyl or

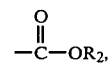

wherein $R_2$ is hydrogen or lower alkyl.

In still another aspect, the invention relates to intermediates of the formula

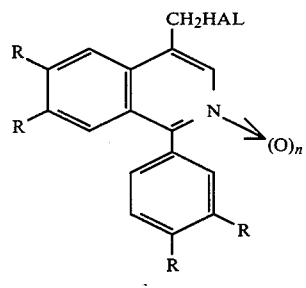

wherein R is lower alkoxy, n is the integer zero or 1, and HAL is hologen.

In yet another aspect, the invention relates to intermediates of the formula

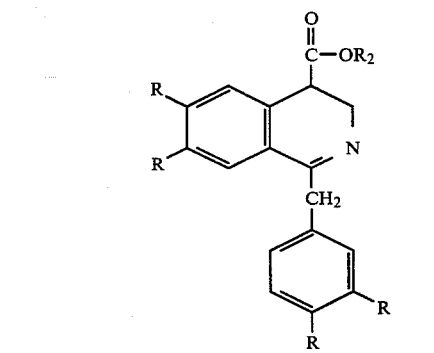

wherein R is lower alkoxy, and $R_2$ is hydrogen or lower alkyl.

DETAILED DESCRIPTION OF THE INVENTION

As used herein, the term "lower alkyl" denotes a straight or branched chain saturated aliphatic hydrocarbon of 1 to 7 carbon atoms, for example, methyl, ethyl, isopropyl, butyl, pentyl, heptyl or the like. The term "lower alkoxy" denotes an alkyl ether group in which the lower alkyl group is as described above, for example, methoxy, ethoxy, propoxy, pentoxy and the like. The term "halogen" denotes all the halogens, that is, bromine, chlorine, fluorine and iodine. Exemplary of halophenyl, lower-alkylphenyl and lower-alkoxyphenyl are 2-bromophenyl, 4-fluorophenyl, 3-methylphenyl, 2-ethylphenyl, 4-propylphenyl, 2-ethoxyphenyl, 4-butoxyphenyl, 3-methoxyphenyl and the like.

The substituted isoquinolines of the invention characterized by the formula

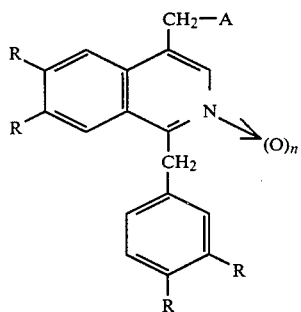

wherein
R is lower alkoxy, n is the integer zero or 1, and
A is

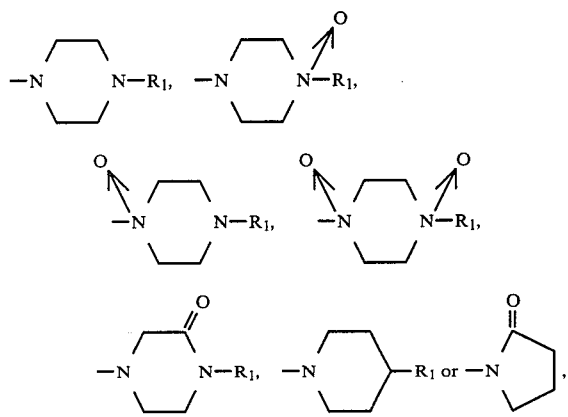

wherein $R_1$ is phenyl, halophenyl lower-alkylphenyl or lower-alkoxyphenyl, and pharmaceutically acceptable acid addition salts thereof, can be prepared as hereinafter described.

A preferred group of compounds of formula I are those wherein A is

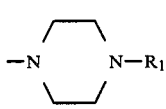

and n is zero.

A still more preferred group of compounds of formula I are those wherein n is zero, and A is

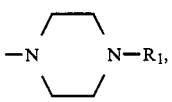

wherein $R_1$ is lower-alkoxyphenyl.

A preferred compound of formula I is 6,7-dimethoxy-1-[(3,4-dimethoxyphenyl)methyl]-4-[[4-(2-methoxyphenyl)-1-piperazinyl]methyl]isoquinoline.

Exemplary of the compounds of formula I are:
6,7-diethoxy-1-[(3,4-diethoxyphenyl)methyl]-4-[[4-(2-methoxyphenyl)-1-piperazinyl]methyl]isoquinoline;
6,7-dimethoxy-1-[(3,4-dimethoxyphenyl)methyl]-4-[[4-(3-chlorophenyl)-1-piperazinyl]methyl isoquinoline;
6,7-dipropoxy-1-[(3,4-dipropoxyphenyl)methyl]-4-[[4-(4-ethylphenyl)-1-piperazinyl]methyl]isoquinoline;
4-[(1-(3,4-diethoxybenzyl)-6,7-diethoxy-4-isoquinolyl)-methyl]-1-(2-methoxyphenyl)-2-piperazinone;
1-[[6,7-diethoxy-1-[(3,4-diethoxyphenyl)methyl]-4-isoquinolinyl]methyl]-2-pyrrolidinone.
1-(3,4-diethoxybenzyl)-6,7-diethoxy-4-[[4'-(2-methoxyphenyl)-1'-piperazinyl]methyl]isoquinoline 4-oxide;
1-(3,4-dimethoxybenzyl)-6,7-dimethoxy-4-[[4'-(2-chlorophenyl)-1'-piperazinyl]methyl]isoquinoline 4'-oxide;
1-(3,4-diethoxybenzyl)-6,7-diethoxy-4-[[4'-(2-methoxyphenyl)-1'-piperazinyl]methyl]isoquinoline 1'-oxide;
1-(3,4-dimethoxybenzyl)-6,7-dimethoxy-4-[[4'-(2-chlorophenyl)-1'-piperazinyl]methyl]isoquinoline 1'-oxide;
1-(3,4-diethoxybenzyl)-6,7-diethoxy-4-[[4'-(2-methoxyphenyl)-1'-piperazinyl]methyl]isoquinoline 1',4'-dioxide;
1-(3,4-dimethoxybenzyl)-6,7-dimethoxy-4-[[4'-(2-chlorophenyl)-1'-piperazinyl]methyl]isoquinoline 1',4' dioxide;
1-(3,4-diethoxybenzyl)-6,7-diethoxy-4-[[4'-(2-methoxyphenyl)-1'-piperazinyl]methyl]isoquinoline 2,4' dioxide;
1-(3,4-dimethoxybenzyl)-6,7-dimethoxy-4-[[4'-(2-chlorophenyl)-1'-piperazinyl]methyl]isoquinoline 2,4' dioxide; and the like.

The compounds of the invention characterized by formula I can be prepared as hereinafter described in Reaction Schemes I and II.

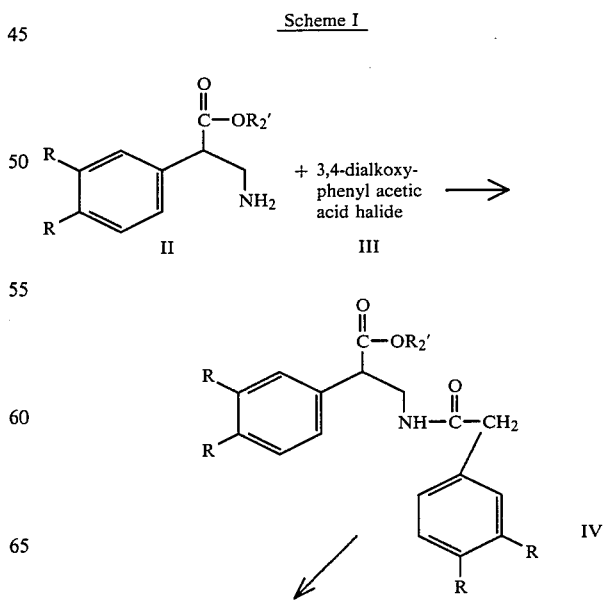

-continued
Scheme I

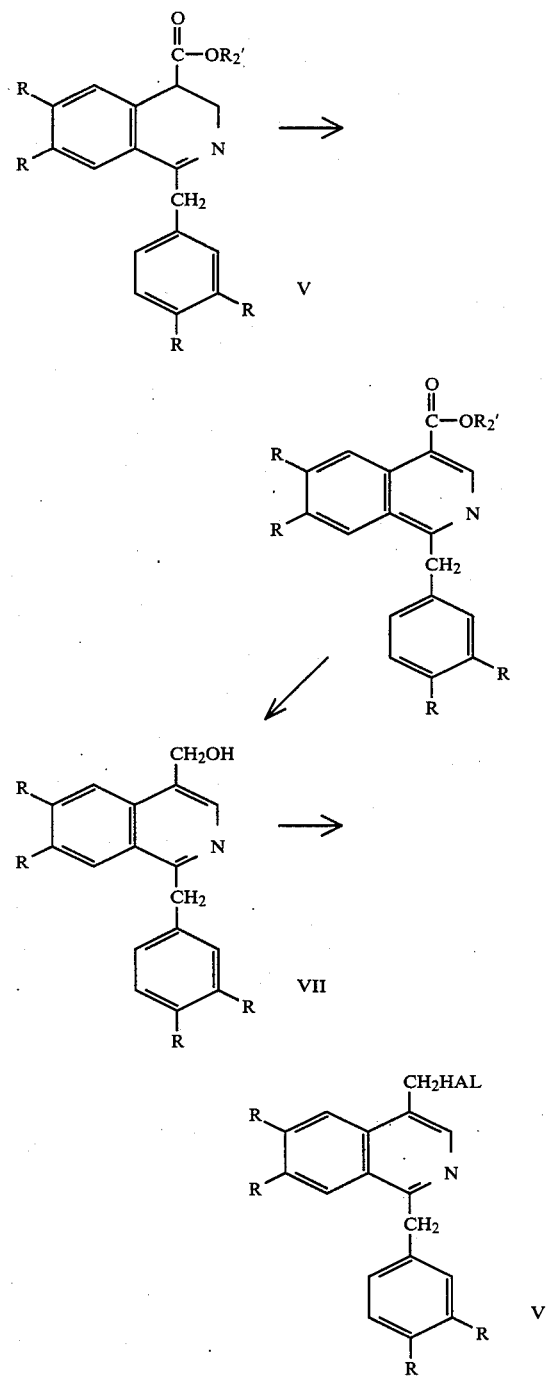

wherein R and n are as previously described, and HAL is halogen and $R_2'$ is lower alkyl.

In Reaction Scheme I, a compound of formula II is condensed with a compound of formula III to yield a desired compound of formula IV. The condensation can be carried out according to known procedures. For example, the condensation can be carried out at a temperature in the range of from about 0° to about 40° C., preferably at 20°, in an inert organic solvent such as methylene chloride or the like and a suitable base, for example, an alkali metal hydroxide such as sodium hydroxide or the like. The resulting compound of formula IV can be recovered according to known procedures from the organic phase, for example, by evaporation or the like.

A compound of formula IV can be cyclized to a compound of formula V utilizing known procedures. More particularly, a compound of formula IV is treated with a cyclizing agent such as phosphorus oxychloride in an inert organic solvent such as acetonitrile or the like. The resulting compound of formula V can be recovered by known procedures, for example, by evaporation or the like.

A compound of formula V can be dehydrogenated to yield a compound of formula VI. The dehydrogenation is carried out according to known procedures. For example, the dehydrogenation can be effected by heating an intimate mixture of a compound of formula V with sulfur to yield the desired compound of formula VI.

A compound of formula VI can be reduced to yield a compound of formula VII according to known procedures. For example, the reduction can be carried out by treating a compound of formula VI, in an inert solvent, with a suitable reducing agent such as sodium bis-(2-methoxyethoxy)-aluminum hydride or the like. The inert solvent can be, for example, toluene, tetrahydrofuran or the like. The resulting compound of formula VII can be recovered by diluting the reaction mixture with water and extracting with an organic solvent such as methylene chloride or the like. Subsequently, the organic solvent is evaporated to yield the desired compound of formula VII.

Alternatively, the ester of formula VI can be converted to the corresponding acid, that is, wherein $R_2'$ is hydrogen, by hydrolysis utilizing, for example, sodium hydroxide or the like. Thereafter, the resulting acid of formula VI, that is, wherein $R_2$ is hydrogen, can be converted to the corresponding alcohol of formula VII utilizing a reducing agent, for example, diborane, in an inert organic solvent, for example, tetrahydrofuran and the like. The resulting compound of formula VII can be recovered by diluting the reaction mixture with water and extracting with an organic solvent such as methylene chloride or the like. Subsequently, the organic solvent is evaporated to yield the desired compound of formula VII.

A compound of formula VII can be converted to the alkyhalide of formula VIII, wherein n is zero, utilizing known procedures. For example, the conversion can be effected by treatment with a thionylhalide in the presence of an organic solvent such as methylene chloride or the like. The resulting compound of formula VIII can be recovered by diluting the resulting reaction mixture with water and extracting with an organic solvent such as methylene chloride or the like. Subsequently, the organic solvent is evaporated to yield the desired compound of formula VIII.

A compound of formula VIIIa can be converted to the corresponding N-oxide of the formula

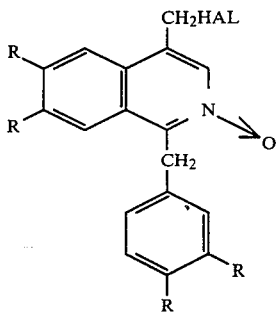
VIIIb utilizing known procedures. More particularly, the N-oxidation can be effected by treating a compound of formula VIIIa with a suitable oxidizing agent, for example, hydrogen peroxide, alkyl hydroperoxides, peracids such as m-chloro-perbenzoic acid, or the like. The N-oxidation can be carried out utilizing known reaction conditions. Thus, the oxidation can be carried out at a temperature in the range of from about 0° to about 35° C., in the presence of an inert organic solvent, for example, methylene chloride or the like. The resulting compound of formula VIIIb can be recovered utilizing known procedures, for example, extraction and evaporation, or the like.

The α-(aminomethyl)-3,4-di-lower-alkoxybenzene acetic acid lower alkyl ester starting materials of formula II are known compounds or can be prepared according to known procedures. Exemplary of the compounds of formula II are:

α-(aminomethyl)-3,4-dimethoxybenzenacetic acid ethyl ester;
α-(aminomethyl)-3,4-diethoxybenzene acetic acid ethyl ester;
α-(aminomethyl)-3,4-dimethoxybenzeneacetic acid methyl ester;
α-(aminomethyl)-3,4-dibutoxybenzene acetic acid propyl ester;
α-(aminomethyl)-3,4-dipropoxybenzene acetic acid methyl ester, and the like.

The 3,4-dialkoxyphenyl acetic acid halide starting materials are known compounds or can be prepared according to known procedures, which include the reaction of the corresponding 3,4-dialkoxyphenyl acetic acid with a thionyl halide such as thionyl chloride in situ. Exemplary of the 3,4-dialkoxyphenyl acetic acid halide compounds are:

3,4-dimethoxyphenyl acetic acid chloride;
3,4-diethoxyphenyl acetic acid bromide;
3,4-dipropoxyphenyl acetic acid chloride
2,4-dipentoxyphenyl acetic acid chloride; and the like.

Scheme II

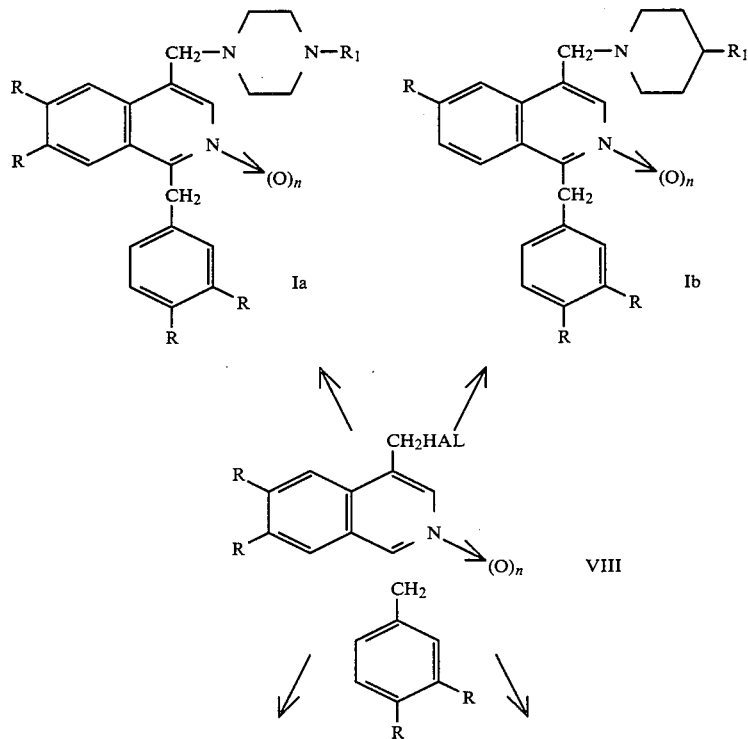

Scheme II

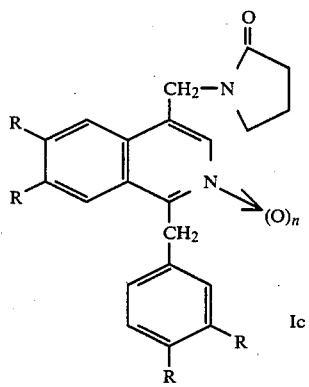 Ic

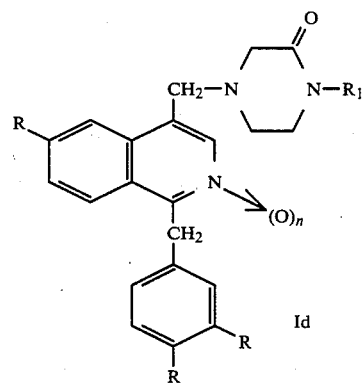 Id wherein R,n,R₁ and HAL are as previously described.

In Reaction Scheme II, a 4-halomethyl-6,7-dialkoxy-1-[(3,4-dialkoxyphenyl)methyl]isoquinoline of formula VIII is converted to a 6,7-dialkoxy-1-[(3,4-dialkoxyphenyl)methyl]-4-[(1-piperazinyl)methyl]isoquinoline of formula Ia by condensing a compound of formula VIII with a piperazine of the formula

 (a)

wherein R₁ is as previously described or a salt thereof.

The piperazines of formula (a) are known compounds or can be prepared according to known procedures. Exemplary of such compounds are: phenyl piperazine, 1-(4-chlorophenyl)piperazine, 1-(4-tolyl)piperazine, 1-(4-ethoxyphenyl)piperazine and the like. The condensation is carried out according to known procedures, for example, by heating at a temperature in the range of from about room temperature to about 100° C. in the presence of an inert solvent such as dimethylsulfoxide, dimethylformamide or the like, and in the presence of a suitable base, for example, an alkali metal hydroxide such as sodium hydroxide, potassium hydroxide or the like, or an organic amine, for example, a trialkylamine such as triethylamine or the like. The desired compound of formula Ia can be recovered utilizing known procedures, for example, dilution with water and filtration or extraction with an organic solvent such as methylene chloride or ethylacetate and subsequent evaporation.

In Reaction Scheme II, a 4-halomethyl-6,7-dialkoxy-1-[(3,4-dialkoxyphenyl)methyl]isoquinoline of formula VIII is converted to a 6,7-dialkoxy-1-[(3,4-dialkoxyphenyl)methyl]-4-[(4-[(1-piperidinyl)methyl]isoquinoline of formula Ib by condensing a compound of formula VIII with a piperidine of the formula

 (b)

wherein R₁ is as previously described, or a salt thereof.

The piperidines of formula (b) are known compounds or can be prepaed according to known procedures. Exemplary of such compounds are: 4-phenyl piperidine, 4-(4-methoxyphenyl) piperidine, 4-(3-tolyl)piperidine, 4-(2-chlorophenyl)piperidine and the like. The condensation can be carried out in a similar manner to that described for the preparation of a compound of formula Ia.

In Reaction Scheme II, a 4-halomethyl-6,7-dialkoxy-1-[(3,4-dialkoxyphenyl)methyl]isoquinoline of formula VIII is converted to a 6,7-dialkoxy-1-[(3,4-dialkoxyphenyl)methyl]-4-[(1-pyrrolidinyl)methyl]isoquinoline of formula Ic by the condensation of a compound of formula VIII with the alkali metal salt of 2-pyrrolidinone, a known compound. The condensation is carried out according to known procedures, for example, by refluxing in an organic solvent such as tetrahydrofuran or the like. The desired compound of formula Ic can be recovered utilizing known procedures, for example, dilution with water, extraction with an organic solvent such as methylene chloride or ethylacetate and subsequent evaporation.

In Reaction Scheme II, a 4-halomethyl-6,7-dialkoxy-1-[(3,4-dialkoxyphenyl)methyl]isoquinoline of formula VIII is converted to a 6,7-dialkoxy-1-[(3,4-dialkoxyphenyl)methyl]-4-[(1-piperazinyl-3-one)methyl]isoquinoline of formula Id by condensing a compound of formula VIII with a piperazinone of the formula

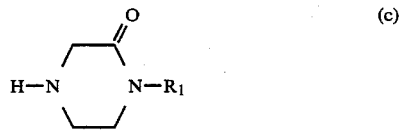 (c)

wherein R₁ is as previously described, or a salt thereof.

The piperazinones of formula (c) are known compounds or can be prepared according to known procedures. Exemplary of such compounds are: 4-(4-methoxyphenyl)-2-piperazinone, 4-(4-tolyl)-2-piperazinone, 4-(3-chlorophenyl)-2-piperazinone and the like. The condensation can be carried out in a similar manner to that described for the preparation of a compound of formula Ia.

The piperazine N-oxides of the compounds of formula Ia can be prepared as described below. More specifically, a compound of formula Ia is treated with a suitable oxidizing agent, for example, hydrogen peroxide, alkyl hydroperoxides, peracids such as m-chloroperbenzoic acid, or the like. The oxidation can be carried out utilizing known reaction conditions. Thus, the oxidation can be carried out at a temperature in the range of from about 0° to about 5° C., in the presence of an inert organic solvent such as methylene chloride or the like. The resulting reaction mixture comprises a mixture of one of each of the correspoonding N-oxides of the formulas

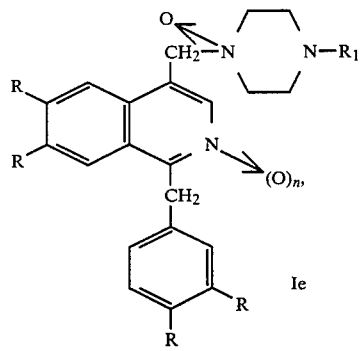

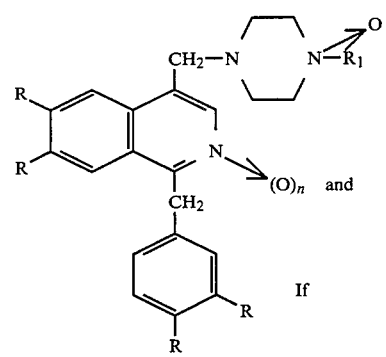

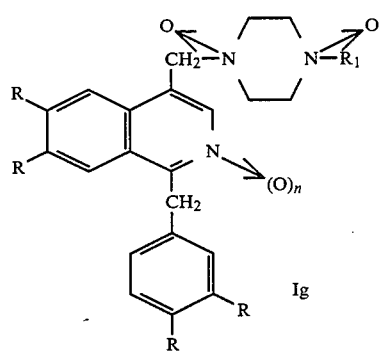

wherein R, $R_1$, and n are as previously described.

Each of the compounds of formulas Ie, If and Ig can be separated from the mixture utilizing conventional methods, for example, chromatography and the like.

Alternatively, a compound of the formula If can be prepared by reacting a compound of formula VIII with a piperazine N-oxide of the formula

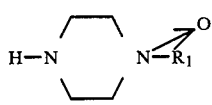 (d)

wherein $R_1$ is as previously described, or a salt thereof.

The reaction conditions for this conversion are the same as those previously described for the preparation of a compound of formula Ia from a compound of formula VIII. The piperazine N-oxides of formula (d) are known compounds or can be prepared according to known procedures. Exemplary of such compounds are: 1-(2-methoxyphenyl)piperazine 1-oxide; 1-(3-chlorophenyl)piperazine 1-oxide; 1-(4-ethylphenyl)piperazine 1-oxide; 1-(2-ethoxyphenyl)piperazine 1-oxide; 1-(3-butylphenyl)piperazine 1-oxide; 1-(2-propoxyphenyl) piperazine 1-oxide; and the like.

The compounds of formula I of the invention form acid addition salts and such salts are also within the scope of this invention. Thus, the compounds of formula I form pharmaceutically acceptable addition salt with, for example, both pharmaceutically acceptable organic and inorganic acids, such as acetic acid, succinic acid, maleic acid, formic acid, methanesulfonic acid, p-toluene-sulfonic acid, hydrochloric acid, hydrobromic acid, nitric acid, phosphoric acid, sulfuric acid and the like. The base compounds of formula I form salts with up to 3 molecules of acid; thus, the base compounds of formula I form hemi-, momo-, di- or tri-acid salts.

The compounds of formula I, as well as their pharmaceutically acceptable acid addition salts, are useful in the treatment and control of cerebrovascular disorders such as stroke, cerebroarteriosclerosis or transient ischemic attacks; myocardial ischemia; and hypertension.

More particularly, a compound of formula I, namely, 6,7-dimethoxy-1-{(3,4-dimethoxyphenyl)methyl}-4-([4-(2-methoxyphenyl)-1-piperazinyl]methyl)isoquinoline (hereinafter referred to as Compound A), showed erythrocyte deformability improving action and selective $\alpha_1$-adrenoceptor blocking action. Furthermore, Compound A inhibited erythrocyte membrane rupture, lipid peroxidation and platelet aggregation. Compound A induced its vasular action through the intracellular pivotal process in vascular contraction, by inhibiting the formation of a $Ca^{++}$-calmodulin and myosin light chain kinase complex. Accordingly, it is completely different from cerebral vasodilative calcium influx blockers such as nifedipine analogues, nimodipine and nicardipine. In contrast to most vasodilators, Compound A was orally long-acting and did not produce tachycardia and orthostatic hypotension.

The decreased vertebral vascular resistance and femoral vascular resistance produced by the compounds of formula I, when administered intravenously, can be demonstrated as hereinafter described.

In anesthetized dogs, Compound A, when 4 doses were given into the femoral vein dose-dependently (0.1-3 mg/kg), decreased vascular resistance of vertebral and femoral arteries, and exerted 1.2- and 1.9-fold potency of respective vetebral and femoral vasodilation as compared to papaverine. Results are set out in Table I and Table II. Compound A slightly and dose-dependently (0.1-3 mg/kg i.v.) lowered both diastolic and systolic blood pressures but did not induce tachycardia due to hypotension. Results are set out in Table I for Compound A as well as other compounds of the invention.

The effects of Compound A on various vascular vessels were compared. Compound A (0.1-1.0 mg/kg i.v.) increased regional cerebral blood flow (parietal cortex) and vertebral blood flow more markedly than femoral muscle, mesenteric vascular and renal blood flows. In agreement with arterial administration, the vertebral vasodilating action of Compound A given i.v. was greater than the internal carotid vasodilating action.

Blood flow rates of both canine vertebral and internal carotid flow rates were equivalent (30 ml/min.). Coronary vasodilating effect of the compound was comparable to its vertebral vasodilating effect.

The decreased vertebral vascular resistance and femoral vascular resistance produced by the compounds of formula I, when administered intraduodenally, can be demonstrated as hereinafter described.

The test compounds in 0.1% sodium carboxymethyl cellulose solution were introduced into the duodenum through an implanted catheter in dogs anesthetized with pentobarbital. Compound A dose-dependently (3, 10 and 30 mg/kg i.d.) decreased the vertebral vascular resistance more extently than femoral vascular resistance. In parallel with the vertebral vasodilation, Compound A moderately lowered diastolic/systolic blood pressure and heart rate. Results are set out in Table I.

The vertebral vasodilating effect of Compound A was more selective and longer lasting than those after its intravenous and intra-arterial administration.

TABLE I

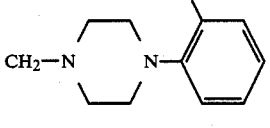

| Compounds | R | 1.0 mg/kg i.v. s-BP/d-BP (Δ mmHg) | 1.0 mg/kg i.v. HR (Δ beats/min) | 10 mg/kg i.d. VVR | 10 mg/kg i.d. FVR | 10 mg/kg i.d. s-BP/d-BP (Δ mmHg) | 10 mg/kg i.d. HR (Δ beats/min) |
|---|---|---|---|---|---|---|---|
| A | 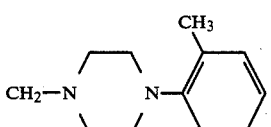 | −30/−41 | −2 | −17 | −9 | −17/−24 | −7 |
| B | 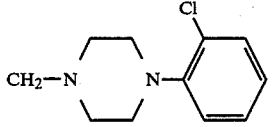 | −16/−23 | 8 | — | — | — | — |
| C | 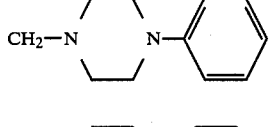 | −15/−16 | 6 | — | — | — | — |
| D |  | −14/−12 | 14 | — | — | — | — |
| E | 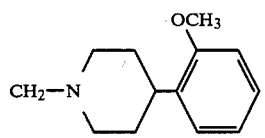 | −6/−4 | 3 | — | — | — | — |
| F | | −4/−4 | 6 | — | — | — | — |
| G | | −24/−32 | 6 | −10 | −8 | −12/−17 | 10 |

TABLE I-continued

[Chemical structure: isoquinoline with 3HCO substituents and OCH3 group, with R position indicated]

| Compounds | R | 1.0 mg/kg i.v. | | Change in % | | 10 mg/kg i.d. | |
|---|---|---|---|---|---|---|---|
| | | s-BP/d-BP (Δ mmHg) | HR (Δ beats/min) | VVR | FVR | s-BP/d-BP (Δ mmHg) | HR (Δ beats/min) |
| H | [CH2-N-pyrrolidinone structure] | −18/−23 | 7 | −3 | −5 | −1/−8 | 18 |
| Papaverine | | −18/−34 | 23 | −11 | −7 | −11/−14 | 15 |

VVR: Vertebral Vascular Resistance
FVR: Femoral Vascular Resistance
BP: Blood Pressure
HR: Heart Rate

TABLE II

Vasodilating Effects of a Compound of the Invention and Papaverine

| Compound | Change in Vertebral vasc. resist. (10 mg/kg i.d.) | | VVR Potency Ratio vs Papaverine (iv) | Change in Femoral vasc. resist. (10 mg/kg i.d.) | | FVR Potency Ratio vs Papaverine (iv) |
|---|---|---|---|---|---|---|
| | % Change | Duration (min) | | % Change | Duration (min) | |
| Papaverine | −11 | 60 | 1.0 | −7 | 40 | 1.0 |
| Compound A | −17 | >180 | 1.23 | −9 | >180 | 1.93 |

A compound of formula I of the invention, as well as a pharmaceutically acceptable acid addition salt thereof, can be incorporated into standard pharmaceutical dosage forms, for example, those which are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene-glycols, and the like. The pharmaceutical preparations can be employed in a solid form, for example, as tablets, troches, suppositories, capsules, or in liquid form, for example, as solutions, suspensions or emulsions. The pharmaceutical adjuvant material can include preservatives, stabilizers, wetting or emulsifying agents, salts to change the osmotic pressure or to act as buffers. The pharmaceuticl dosage forms can also contain other therapeutically active materials.

The quantity of active medicament, that is, a compound of formula I, or an equivalent quantity of a salt thereof, which can be present in any of the above-described dosage forms is variable. It is preferred however, to provide capsules or tablets containing from about 30 mg. to about 300 mg. of the base of a compound of formula I or an equivalent amount of a medicinally or pharmaceutically acceptable acid addition salt thereof. For parenteral administration, it is preferred to provide a solution containing from about 10 mg./ml. to about 50 mg./ml. of the base of a compound of formula I, or an equivalent quantity of a salt thereof. The frequency with which any such dosage form will be administered to a warm-blooded animal will vary, depending upon the quantity of active medicament present therein and the needs and requirements of the host. Under ordinary circumstances, however, up to about 10 mg./kg. of a compound of formula I, or an equivalent quantity of a salt thereof, can be administered daily in several oral dosages. It is to be understood, however, that the dosages set forth herein are exemplary only and that they do not, to any extent, limit the scope of this invention.

The examples which following further illustrate the invention. All temperatures are in degrees centigrade unless otherwise stated.

EXAMPLE 1

Preparation of 2-(3,4-dimethoxyphenyl)-3-{{[(3,4-dimethoxyphenyl)-methyl]carbonyl}amino}propanoic acid ethyl ester A mixture of 289 g of alpha-(aminomethyl)-3,4-dimethoxybenzeneacetic acid ethyl ester hydrochloride, 1000 ml of methylene chloride and 1000 ml of water was cooled to 0° and adjusted to pH 9.0 with 4N sodium hydroxide. A solution of 1000 ml of methylene chloride and 3,4-dimethoxyphenyl acetic acid chloride [previously prepared by the action of 400 ml of thionyl chloride on 215 g of 3,4-dimethoxyphenyl acetic acid in 500 ml of toluene at 50° for 1 hour and evaporation to dryness] was added concurrently with 4N sodium hydroxide maintaining a pH of 7.0–8.0. Upon completion of the acid chloride addition, the pH was maintained at 9.0 for 1 hour followed by acidification to pH 1.0 with 6N hydrochloric acid. The layers were separated and the aqueous layer extracted once with methylene chloride. The combined organic layers were washed once with exceess saturated sodium bicarbonate solution, dried over sodium sulfate and evaporated in vacuo to give 430 g of 2-(3,4-dimethoxyphenyl)-3-{{[(3,4-dimethoxyphenyl)methyl]carbonyl}amino}propanoic acid ethyl ester as an oil.

EXAMPLE 2

Preparation of 2-(3,4-dimethoxyphenyl)-3-{{[(3,4-dimethoxyphenyl)methyl]carbonyl}amino}propanoic acid A mixture of 18.4 g of 2-(3,4-dimethoxyphenyl)-3-{{[(3,4-dimethoxyphenyl)methyl]carbonyl}amino}propanoic acid ethyl ester, 50 ml of ethanol, and 65 ml of 10% sodium hydroxide was refluxed for 2 hours, concentrated to remove ethanol, and diluted with water. The aqueous layer was washed with ethyl acetate, acidified with excess 6N hydrochloric acid, and the product was extracted with ethyl acetate, dried, and evaporated. Trituration of the residue with ether provided 10.9 g of insoluble 2-(3,4-dimethoxyphenyl)3-{{[(3,4-dimethoxyphenyl)methyl]carbonyl}amino}propanoic acid, mp 151°–153°. Crystallization from ethyl acetate gave the analytical sample, mp 150°–152°.

Analysis Calculated for $C_{21}H_{25}NO_7$: C, 62.52; H, 6.25; N, 3.47. Found: C, 62.41; H, 6.26; N, 3.45.

EXAMPLE 3

Preparation of 2-(3,4-dimethoxyphenyl)-3-{{[(3,4-dimethoxyphenyl)methyl]carbonyl}amino}propanoic acid methyl ester A solution of 23.3 g of 2-(3,4-dimethoxyphenyl)-3-{{[(3,4-dimethoxyphenyl)methyl]carbonyl}amino}propanoic acid and 15.5 ml of concentrated sulfuric acid in 300 ml of methanol was refluxed for 6 hours and evaporated to dryness. The residue was partitioned between ethyl acetate and dilute sodium bicarbonate solution and the organic layer was dried and evaporated to give 15.5 g of crude 2-(3,4-dimethoxyphenyl)-3-{{[(3,4-dimethoxyphenyl)methyl]carbonyl}amino}propanoic acid methyl ester. Crystallization from ethyl acetate provided the analytical sample, mp 92°–93°.

Analysis Calculated for $C_{22}H_{27}NO_7$: C,63.30; H, 6.52; N, 3.36. Found: C, 63.35; H, 6.52; N, 3.31.

EXAMPLE 4

Preparation of 3,4-dihydro-6,7-dimethoxy-1-[(3,4-dimethoxyphenyl)methyl]-4-isoquinolinecarboxylic acid ethyl ester hydrochloride A mixture of 430 g (1.0 mole) of 2-(3,4-dimethoxyphenyl)-3-{{[(3,4-dimethoxyphenyl)methyl]carbonyl}amino}propanoic acid ethyl ester, 4300 ml of acetonitrile and 430 g of phosphorus oxychloride was refluxed for 1 hour and evaporated in vacuo. Crystallization of the residue from ethanol provided 399 g of the hydrochloride 3,4-dihydro-6,7-dimethoxy-1-[(3,4-dimethoxyphenyl)methyl]-4-isoquinoline carboxylic acid ethyl ester as a yellow solid, mp 213°–214° dec.

Analysis Calculated for $C_{23}H_{27}NO_6.HCl$: C,61.40; H,6.27; N,3.11; Cl,7.88. Found: C,61.11; H,6.48; N,3.06; Cl,7.89.

EXAMPLE 5

Preparation of 3,4-dihydro-6,7-dimethoxy-1-[(3,4-dimethoxyphenyl)methyl]-4-isoquinoline carboxylic acid methyl ester, hydrochloride.

The hydrochloride of 3,4-dihydro-6,7-dimethoxy-1-[(3,4-dimethoxyphenyl)methyl]-4-isoquinoline carboxylic acid methyl ester was prepared by treating 2-(3,4-dimethoxyphenyl)-3-{{[(3,4-dimethoxyphenyl)methyl]carbonyl}amino}propanoic acid methyl ester via the method described for the preparation of 3,4-dihydro-6,7-dimethoxy-1-[(3,4-dimethoxyphenyl)methyl]-4-isoquinolinecarboxylic acid ethyl ester hydrochloride. Crystallization from methanol provided analytically pure 3,4-dihydro6,7-dimethoxy-1-[(3,4-dimethoxyphenyl)methyl]-4-isoquinolinecarboxylic acid methyl ester, hydrochloride, mp 199°–200°.

Analysis Calculated for $C_{22}H_{25}NO_6.HCl$: C,60.62; H,6.01; N,3.21. Found: C,60.56; H,6.08; N,3.17.

EXAMPLE 6

Preparation of 3,4-dihydro-6,7-dimethoxy-1-[(3,4-dimethoxyphenyl)methyl]-4-isoquinoline carboxylic acid.

A mixture of 3 g of 3,4-dihydro-6,7-dimethoxy-1-[(3,4-dimethoxyphenyl)methyl]-4-isoquinolinecarboxylic acid ethyl ester hydrochloride in 15 ml of ethanol and 15 ml of 10% sodium hydroxide was refluxed for one hour and concentrated to remove ethanol. The aqueous residue was adjusted to pH 6.7 with 6N hydrochloric acid and the product was recovered by filtration. Drying gave 1.9 g of 3,4-dihydro-6,7-dimethoxy-1-[(3,4-dimethoxyphenyl)methyl]-4-isoquinoline mp 154°–155°.

EXAMPLE 7

Preparation of 6,7-dimethyoxy-1-[(3,4-dimethoxyphenyl)methyl]-4-isoquinolinecarboxylic acid ethyl ester The free base of 3,4-dihydro-6,7-dimethoxy-1-[(3,4-dimethoxyphenyl)methyl]-4-isoquinolinecarboxylic acid ethyl ester hydrochloride was prepared immediately prior to use by partitioning 135 g of 3,4-dihydro-6,7-dimethoxy-1-[(3,4-dimethoxyphenyl)methyl-4-isoquinolinecarboxylic acid ethyl ester hydrochloride between methylene chloride and saturated sodium bicarbonate solution, drying over sodium sulfate, and evaporating from ether to give an ether solvated white solid. Sublimed sulfur (10.5 g) was added and the resulting mixture was heated under a slow stream of argon at 150° with evolution of hydrogen sulfide until a clear molten mass was obtained. The mixture was cooled to about 80°, dissolved in hot ethanol, and diluted with four parts of ether. The chilled mixture was filtered to give 98.6 g of 6,7-dimethoxy-1-[(3,4-dimethoxyphenyl)methyl]-4-isoquinolinecarboxylic acid ethyl ester as a white solid, mp 117°–119°. Recrystallization from ether provided the analytical sample, mp 117°–119°.

Analysis Calculated for $C_{23}H_{25}NO_6$: C, 67.14; H, 6.12; N, 3.40. Found: C, 67.17; H, 6.19; N, 3.53.

EXAMPLE 8

Preparation of
6,7-dimethoxy-1-[(3,4-dimethoxyphenyl)methyl]-4-isoquinolinecarboxylic acid methyl ester, and its hydrobromide salt A mixture of 3.9 g of 3,4-dihydro-6,7-dimethoxy-1-[(3,4-dimethoxyphenyl)methyl]-4-isoquinoline carboxylic acid methyl ester, hydrochloride, 100 ml of decalin and 2 g of 10% palladium on carbon was stirred and refluxed for 2 hours. The cooled mixture was diluted with water, acidified with 6N hydrochloric acid, and the catalyst was removed by filtration. The aqueous solution was washed with ether, made basic with excess ammonium hydroxide, and the product was extracted with ethyl acetate, dried, and evaporated to give 4.1 g of crude 6,7-dimethoxy-1-[(3,4-dimethoxyphenyl)methyl]-4-isoquinolinecarboxylic acid methyl ester. Crystallization from ether provided the analytically pure material, mp 127°–128°.

Analysis Calculated for $C_{22}H_{23}NO_6$: C, 66.49; H, 5.83; N, 3.52. Found: C, 66.79; H, 6.00; N, 3.51.

Free base 6,7-dimethoxy-1-[(3,4-dimethoxyphenyl)methyl]-4-isoquinolinecarboxylic acid methyl ester (1.5 g) in ethanol was treated with a solution of ethanolic hydrobromic acid and the solids were recovered by filtration. Recrystallization from ethanol provided 1.8 g of analytically pure hydrobromide salt, mp 188°–189°.

Analysis Calculated for $C_{22}H_{23}NO_6 \cdot HBr$: C, 55.24; H, 5.05; N, 2.93. Found: C, 55.19; H, 5.08; N, 2.90.

EXAMPLE 9

Preparation of
6,7-dimethoxy-1-[(3,4-dimethoxyphenyl)methyl]-4-isoquinolinecarboxylic acid, and its hydrobromide salt 2.0 g of 6,7-dimethoxy-1-[(3,4-dimethoxyphenyl)methyl]-4-isoquinolinecarboxylic acid methyl ester, 20 ml of ethanol, and 20 ml of 10% sodium hydroxide was stirred and refluxed for 2 hours and evaporated to remove ethanol. The residue, in water, was acidified with hydrobromic acid, extracted three times with chloroform, dried, and evaporated. Crystallization of the residue from acetonitrile provided 1.8 g of crude hydrobromide salt, mp 210°–211°.

A portion of the crude hydrobromide salt in aqueous ammonium hydroxide was adjusted to pH 6.7 with 6N hydrochloric acid and the solids recovered by filtration giving analytically pure free base 6,7-dimethoxy-1-[(3,4-dimethoxyphenyl)methyl]-4-isoquinolinecarboxylic acid, mp 235°–236°.

Analysis Calculated for $C_{21}H_{21}NO_6$: C, 65.78; H, 5.52; N, 3.65. Found: C, 65.72; H, 5.35; N, 3.47.

EXAMPLE 10

Preparation of
6,7-dimethoxy-1-[(3,4-dimethoxyphenyl)methyl]-4-isoquinoline methanol, and its hydrobromide salt A slurry of 41.1 g of 6,7-dimethoxy-1-[(3,4-dimethoxyphenyl)methyl]-4-isoquinolinecarboxylic acid ethyl ester in 250 ml of dry tetrahydrofuran was chilled to 0° and treated dropwise over 30 minutes with 62.8 ml of 3.5 M sodium bis-(2-methoxyethoxy)aluminum hydride in toluene solution. After stirring at 0° for three hours, 60 ml of saturated aqueous sodium sulfate solution was cautiously added and the mixture was stirred until granular. The supernatant solution was decanted, the residue was extracted with warm methylene chloride, and the combined organic solutions were evaporated in vacuo. The residue was dissolved in methylene chloride, washed with water, dried over sodium sulfate, and concentrated. Crystallization from methylene chloride/ethyl acetate provided 26.7 g of 6,7-dimethoxy-1-[(3,4-dimethoxyphenyl)methyl]-4-isoquinoline methanol as a white solid, mp 140°–146°.

A portion of base 6,7-dimethoxy-1-[(3,4-dimethoxyphenyl)methyl]-4-isoquinoline methanol in ethanol was treated with 1.1 molar equivalent of ethanolic hydrobromic acid solution and filtered to give analytically pure hydrobromide salt, mp 210°–212°.

Analysis Calculated for $C_{21}H_{23}NO_5 \cdot HBr$: C, 56.01; H, 5.37; N, 3.11. Found: C, 56.10; H, 5.26; N, 3.06.

EXAMPLE 11

Preparation of
4-chloromethyl-6,7-dimethoxy-1-[(3,4-dimethoxyphenyl)methyl]isoquinoline A cold mixture of 26.8 g of 6,7-dimethoxy-1-[(3,4-dimethoxyphenyl)methyl]-4-isoquinoline methanol in 600 ml of methylene chloride was treated dropwise with 27 ml of thionyl chloride over 15 minutes. The cooling bath was removed and the solution was allowed to stir at ambient temperature for 3 hours after which the volatiles were removed in vacuo. The residue was mixed with methylene chloride and water followed by careful addition of excess sodium bicarbonate. The organic layer was separated, dried over sodium sulfate, evaporated, and crystallized from ethyl acetate to give 23.1 g of 4-chloromethyl-6,7-dimethoxy-1-[(3,4-dimethoxyphenyl)methyl]isoquinoline as a yellow solid, mp 153° dec. Recrystallization from ethyl acetate provided the analytically pure material, mp 153° dec.

Analysis Calculated for $C_{21}H_{22}ClNO_4$: C, 65.03; H, 5.72; N, 3.61; Cl, 9.14. Found: C, 64.74; H, 5.82; N, 3.91; Cl, 9.20.

EXAMPLE 12

Preparation of
6,7-dimethoxy-1-[(3,4-dimethoxyphenyl)methyl]-4-[(4-phenyl-1-piperazinyl)methyl]isoquinoline, and its dihydrochloride, hemi-hydrate, salt A mixture of 5.0 g of 4-chloromethyl-6,7-dimethoxy-1-[(3,4-dimethoxyphenyl)methyl]isoquinoline, 2.1 g of phenyl piperazine, and 2.63 g of triethylamine in 50 ml of dimethylsulfoxide was heated at 80° for one hour under argon and then the cooled mixture was diluted with water. The solids were recovered by filtration, dissolved in methylene chloride and washed with saturated sodium bicarbonate, dried over sodium sulfate, charcoaled, and evaporated. The residue was crystallized from ethanol giving 5.3 g of 6,7-dimethoxy-1-[(3,4-dimethoxyphenyl)methyl]-4-[(4-phenyl-1-piperazinyl)methyl]isoquinoline, mp 183°–184°. Recrystallization from ethanol provided the analytical sample, mp 183°–184°.

Analysis Calculated for $C_{31}H_{35}N_3O_4$: C, 72.49; H, 6.87; N, 8.18. Found: C, 72.30; H, 6.85; N, 8.21.

Free base 6,7-dimethoxy-1-[(3,4-dimethoxyphenyl)methyl]-4-[(4-phenyl-1-piperazinyl)methyl]isoquinoline (5.0 g) in 50 ml of warm ethanol was treated with 2 molar equivalents of ethanolic hydrochloric acid solution and the resulting solid was recovered by filtration. Recrystallization from 95% ethanol and drying of the product at 80°/0.1 mm over phosphorous pentoxide provide 5.3 g of the analytically pure hydrated dihydrochloride salt, 217°–219° dec.

Analysis Calculated for $C_{21}H_{35}N_3O_4 \cdot 2HCl \cdot 0.5\ H_2O$: C, 62.52; H, 6.43; N, 7.06; Cl, 11.91; $H_2O$, 1.51. Found: C, 62.59; H, 6.33; N, 7.05; Cl, 12.23; $H_2O$, 1.49.

EXAMPLE 13

Preparation of 6,7-dimethoxy1-{(3,4-dimethoxyphenyl)methyl}-4-[[4-(2-chlorophenyl)-1-piperazinyl]methyl]isoquinoline, and its dihydrochloride, 1.5 molar hydrate, salt A mixture of 5.0 g of 4-chloromethyl-6,7-dimethoxy-1-[(3,4-dimethoxyphenyl)methyl]isoquinoline, 3.5 g of 1-(ortho-chlorophenyl)piperazine dihydrochloride, and 5.26 g of triethylamine in 50 ml of dimethylsulfoxide was heated at 80° for one hour under argon and then the cooled mixture was diluted with water. The solids were recovered by filtration, dissolved in methylene chloride and washed with saturated sodium bicarbonate, dried over sodium sulfate, charcoaled, and evaporated. The residue was crystallized from ethanol giving 5.9 g of 6,7-dimethoxy-1-{(3,4-dimethoxy)methyl}-4-[[4-(2-chlorophenyl)-1-piperazinyl]methyl]isoquinoline as a tan solid, mp 141°–142°. Recrystallization from ethanol provided the analytical sample, mp 141°–142°.

Analysis Calculated for $C_{31}H_{34}ClN_3O_4$: C, 67.94; H, 6.25; N, 7.67; Cl, 6.47. Found: C, 67.95; H, 6.34; N, 7.77; Cl, 6.69.

Free base 6,7-dimethoxy-1-{(3,4-dimethoxyphenyl)methyl}-1-[[4-(2-chlorophenyl)-1-piperazinyl]methyl]isoquinoline (5.2 g) in 50 ml of warm ethanol was treated with 2.2 molar equivalents of ethanolic hydrochloric acid solution and the resulting solid was recovered by filtration. Recrystallization from 95% ethanol provided 6.0 g of analytically pure hydrated dihydrochloride salt, mp 227°–228°.

Analysis Calculated for $C_{31}H_{34}ClN_3O_4 \cdot 2HCl \cdot 1.5\ H_2O$: C, 57.46; H, 6.07; N, 6.48; Cl, 16.41; $H_2O$, 4.17. Found: C, 57.22; H, 5.83; N, 6.43; Cl, 16.02; $H_2O$, 4.21.

EXAMPLE 14

Preparation of 6,7-dimethoxy-1-{(3,4-dimethoxyphenyl)methyl}-4-[[4-(2-methylphenyl)-1-piperazinyl]methyl]isoquinoline, and its dihydrochloride, 1.25 molar hydrate, salt A mixture of 5.0 g of 4-chloromethyl-6,7-dimethoxy-1-[(3,4-dimethoxyphenyl)methyl]isoquinoline, 3.24 g of 1-(ortho-tolyl)piperazine dihydrochloride, and 5.26 g of triethylamine in 50 ml of dimethylsulfoxide was heated at 80° for one hour under argon and then the cooled mixture was diluted with water. The solids were recovered by filtration, dissolved in methylene chloride and washed with saturated sodium bicarbonate, dried over the sodium sulfate, charcoaled, and evaporated. The residue was crystallized from ethanol giving 5.8 g of 6,7-dimethoxy-1-{(3,4-dimethoxyphenyl)methyl}-4-[[4-(2-methylphenyl)-1-piperazinyl]methyl]isoquinoline, as a yellow solid, mp 154°–156°. Recrystallization from ethanol provided the analytical sample, mp 154°–156°.

Analysis Calculated for $C_{32}H_{37}N_3O_4$: C, 72.84; H, 7.07; N, 7.96. Found: C, 72.94; H, 6.97; N, 7.93.

Free base 6,7-dimethoxy-1-{(3,4-dimethoxyphenyl)methyl}-4-[[4-(2-methylphenyl)-1-piperazinyl]methyl]isoquinoline (5.2 g) in 50 ml of warm ethanol was treated with 2.2 molar equivalents of ethanolic hydrochloric acid solution and the resulting solid was recovered by filtration. Recrystallization from 95% ethanol provided 5.3 g of analytically pure hydrated dihydrochloride salt, mp 227°–229°.

Analysis Calculated for $C_{32}H_{37}N_3O_4 \cdot 2HCl \cdot 1.25\ H_2O$: C, 61.71; H, 6.68; N, 6.75; Cl, 11.38; $H_2O$, 3.61. Found: C, 61.43; H, 6.36; N, 6.64; Cl, 11.32; $H_2O$, 3.87.

EXAMPLE 15

Preparation of 6,7-dimethoxy-1-{(3,4-dimethoxyphenyl)methyl}-4-[[4-(2-methoxyphenyl)-1-piperazinyl]methyl]isoquinoline, and its dihydrobromide salt A mixture of 10.0 g of 4-chloromethyl-6,7-dimethoxy-1-[(3,4-dimethoxyphenyl)methyl]isoquinoline, 5.5 g of 1-(2-methoxyphenyl)piperazine, and 7.6 ml of triethylamine in 100 ml of dimethylsulfoxide was heated at 80° for one hour under argon. The cooled solution was then diluted with water and extracted with methylene chloride. The organic layer was washed with sodium bicarbonate solution, dried over sodium sulfate, charcoaled, and evaporated. The residue was crystallized from ethanol to give 11.1 g of 6,7-dimethoxy-1-{(3,4-dimethoxyphenyl)methyl}-4-[[4-(2-methoxyphenyl)-1-piperazinyl]methyl]isoquinoline as a yellow solid, mp 117°–119°.

Free base 6,7-dimethoxy-1-{(3,4-dimethoxyphenyl)methyl}-4-[[4-(2-methoxyphenyl)-1-piperazinyl]methyl]isoquinoline (11.0 g) in 150 ml of warm ethanol was treated with 2 molar equivalents of ethanolic hydrobromic acid solution and the resulting solid was recovered by filtration. Recrystallization from 95% ethanol and drying of the resulting solid at 90°/0.1 mm over phosphorus pentoxide provided 14.0 g of the analytically pure dihydrobromide salt, mp 222°–223°.

Analysis Calculated for $C_{32}H_{37}N_3O_5 \cdot 2HBr$: C, 54.48; H, 5.57; N, 5.96; Br, 22.65. Found: C, 54.34; H, 5.33; N, 5.85; Br, 22.73.

EXAMPLE 16

Preparation of 6,7-dimethoxy-1-{(3,4-dimethoxyphenyl)methyl}-4-[[4-(4-methoxyphenyl)-1-piperazinyl]methyl]isoquinoline, and its dihydrochloride salt A mixture of 1.16 g of 4-chloromethyl-6,7-dimethoxy-1-[(3,4-dimethoxyphenyl)methyl]isoquinoline, 0.8 of 1-(para-methoxyphenyl)piperazine hydrochloride, and 1.3 ml of triethylamine in 10 ml dimethylsulfoxide was heated at 80° for one hour under argon. The cooled solution was then diluted with water and extracted with methylene chloride. The organic layer was washed with sodium bicarbonate solution, dried over sodium sulfate, charcoaled, and evaporated. The residue was crystallized from ethanol to give 1.3 g of 6,7-dimethoxy-1-{(3,4-dimethoxyphenyl)methyl}-4-[[4-methoxyphenyl)-1-piperazinyl]methyl]isoquinoline as a yellow solid, mp 176°–177°. Recrystallization from ethanol provided the analytical sample, mp 176°–177°.

Analysis Calculated for $C_{32}H_{37}N_3O_5$: C, 70.69.; H, 6.86; N, 7.73. Found: C, 70.99; H, 6.81; N, 7.80.

Free base 6,7-dimethoxy-1-{(3,4-dimethoxyphenyl)methyl}-4-[[4-(4-methoxyphenyl)-1-piperazinyl]methyl]isoquinoline (0.9 g) was slurried in warm ethanol and treated with 2.2 molar equivalents of ethanolic hydrochloric acid solution and the resulting solid was recovered by filtration. Recrystallization from methanol/ethanol provided the analytically pure dihydrochloride salt, mp 240°–241° dec.

Analysis Calculated for $C_{32}H_{37}N_3O_5.2HCl$: C, 62.34; H, 6.38; N, 6.82; Cl, 11.50. Found: C, 62.15; H, 6.26; N, 6.94; Cl, 11.63.

EXAMPLE 17

Preparation of 6,7-dimethoxy-1(3,4-dimethoxyphenyl)methyl-4-[(4-phenyl-1-piperidinyl)-methyl]isoquinoline, and its dihydrochloride, 1.75 ; molar hydrate, salt A mixture of 5.0 g of 4-chloromethyl-6,7-dimethoxy-1-[(3,4-dimethoxyphenyl)methyl]isoquinoline, 2.1 g of 4-phenylpiperidine, and 2.63 g of triethylamine in 50 ml of dimethylsulfoxide was heated at 80° for one hour under argon and then the cooled mixture was diluted with water. The solids were recovered by filtration, dissolved in methylene chloride and washed with saturated sodium bicarbonate, dried over sodium sulfate, charcoaled, and evaporated. The residue was crystallized from ethanol giving 5.3 g of 6,7-dimethoxy-1-(3,4-dimethoxyphenyl)methyl-4-[(4-phenyl-1-piperidinyl)-methyl]isoquinoline, mp 143°–145°. Recrystallization from ethanol provided the analytical sample, mp 143°–145°.

Analysis Calculated for $C_{32}H_{36}N_2O_4$: C, 74.97; H, 7.08; N, 5.46. Found: C, 75.19; H, 6.98; N, 5.54.

Free base 6,7-dimethoxy-1-(3,4-dimethoxyphenyl)-methyl-4-[(4-phenyl-1-piperidinyl)methyl]isoquinoline (5.0 g) in 50 ml of water ethanol was treated with 2 molar equivalents of ethanolic hydrochloric acid solution and the resulting solid was recovered by filtration. Recrystallization from 95% ethanol provided 5.5g of analytically pure hydrated dihydrochloride salt, mp 223°–224°.

Analysis Calculated for $C_{32}H_{36}N_2O_4.2HCl.1.75\ H_2O$: C, 62.28; H, 6.78; N, 4.54; Cl, 11.49; $H_2O$, 5.10. Found: C, 62.28; H, 6.84; N, 4.40; Cl, 11.64; $H_2O$, 5.28.

EXAMPLE 18

Preparation of 6,7-dimethoxy-1-{(3,4-dimethoxyphenyl)methyl}-4-[[4-(2-methoxyphenyl)-1-piperidinyl]methyl]isoquinoline, and its dihydrochloride, 0.3 molar hydrate, salt A mixture of 5.0 g of 4-chloromethyl-6,7-dimethoxy-1-[(3,4-dimethoxyphenyl)methyl]isoquinoline, 2.49 g of 4-(2-methoxyphenyl)piperidine, and 2.63 g of triethylamine in 50 ml of dimethylsulfoxide was heated at 80° for one hour under argon and then the cooled solution was diluted with water and extracted with methylene chloride. The organic layer was washed with sodium bicarbonate solution, dried over sodium sulfate, charcoaled, and evaporated to give 7.0 g of 6,7-dimethoxy-1-}(3,4-dimethoxyphenyl)methyl}-4-[[4-(2-methoxyphenyl)-1-piperidinyl]-1-piperidinyl]methyl]isoquinoline as a yellow foam.

Free base 6,7-dimethoxy-1-{(3,4-dimethoxyphenyl)-methyl}-4-[[4-(2-methoxyphenyl)-1-piperidinyl]methyl]isoquinoline (7.0 g) in 50 ml of warm ethanol was treated with 2.2 molar equivalents of ethanolic hydrochloric acid solution and the resulting solid was recovered by filtration. Recrystallization from 95% ethanol provided 5.5 g of analytically pure hydrated dihydrochloride salt, mp 229°–231°dec.

Analysis Calculated for $C_{33}H_{38}N_2O_5.\ 2HCl.0.3\ H_2O$: C, 63.83; H, 6.59; N, 4.51; Cl, 11.52; $H_2O$, 0.86. Found: C, 63.86; H, 6.24; N, 4.55; Cl, 11.29; $H_2O$, 0.86.

EXAMPLE 19

Preparation of 1-{[6,7-dimethoxy-1-[(3,4-dimethoxyphenyl)methyl]-4-isoquinolinyl]methyl}-2-pyrrolidinone, and its hydrochloride salt A mixture of 1.4 g of 2-pyrrolidinone, 0.66 g of 60% sodium hydride in oil dispersion, and 175 ml of dried and distilled tetrahydrofuran was stirred and refluxed for one hour under argon. Compound 4-chloromethyl-6,7-dimethoxy-1-[(3,4-dimethoxyphenyl)methyl]isoquinoline, (5.8 g) was then added and reflux was continued for 18 hours. A fresh suspension of sodium pyrrolidinone (prepared from 0.7 g of 2-pyrrolidinone and 0.33 g of 60% sodium hydride in tetrahydrofuran as above) was added and reflux was continued for an additional 24 hours after which the mixture was evaporated to dryness and partitioned between methylene chloride and water. The organic phase was dried over sodium sulfate, evaporated, and the residue was extracted with absolute ethanol, charcoaled, and filtered. Evaporation of the ethanol solution gave 5.3 g of crude 1-{[6,7-dimethoxy-1-[(3,4-dimethoxyphenyl)methyl]-4-isoquinolinyl]methyl}-2-pyrrolidinone as a yellow foam.

Crude 1-{[6,7-dimethoxy-1-[(3,4-dimethoxyphenyl)-methyl]-4-isoquinolinyl]methyl}-2-pyrrolidinone (5.3 g) in 50 ml of absolute ethanol was treated with 1.2 molar equivalents of ethanolic hydrochloric acid solution and the mixture was clarified by filtration through Celite. Dilution with ether provided 4 g of colorless solid, mp 214°–215° dec.

Analysis Calculated for $C_{25}H_{28}N_2O_5.HCl$: C, 63.49; H, 6.18; N, 5.92; Cl, 7.50. Found: C, 63.16; H, 6.20; N, 5.76; Cl, 7.58.

EXAMPLE 20

Preparation of 2bis(phenylmethylamino]-N-(2-methoxyphenyl)acetamide

To a stirred solution of 28.1 g of 2-chloro-N-(2-methoxyphenyl)acetamide (C.A. 50,8730i) in 200 ml toluene was added 58.3 g of dibenzylamine and refluxed for 48 hours. After separation of dibenzylamine hydrochloride, the solvent was removed from the reaction mixture. Crystallization of the residue from isopropylether gave 41.9 g colorless crystals of 2bis(phenylmethyl)amino]-N-(2-methoxyphenyl)acetamine, mp 92°–94°.

EXAMPLE 21

Preparation of N,N-dibenzyl-N'-(2-methoxypheny)-ethylenediamine

To a stirred slurry of 11 g of lithium aluminum hydride in 250 ml anhydrous THF under nitrogen was added dropwise a solution of 43.6 g of 2-[bis(phenylmethyl)amino]-N-(2-methoxyphenyl)acetamide in 500 ml anhydrous tetrahydrofuran and stirred overnight at room temperature. After cooling to 0°, the mixture was treated cautiously in succession with 50 ml of water. The granular precipitate was separated by filtration and washed several times with methylene chloride. The filtrate was evaporated to dryness, the residue dissolved in either and the organic phase extracted with 3 N hydrochloric acid. the water phase was made alkaline with 3 N sodium hydroxide and the base extracted with methylene chloride. The organic layer was washed with water, dried over magnesium sulfate and evaporated at reduced pressure. The crude syrup (36.9 g) was chromatographed on silica gel column packed in methylene chloride. Elution with methylene chloride provided N,N-dibenzyl-N'-(2-methoxyphenyl)ethylenediamine (22.8 g) in the form of an oil.

EXAMPLE 22

Preparation of 4-benzyl-1-(2-methoxyphenyl)-2-piperazinone

To a stirred solution of 21.6 g of N,N-dibenzyl-N'-(2-methoxyphenyl)-ethylenediamine in 400 ml methylene chloride was added 12.9 g of sodium carbonate. To this mixture, a solution of 8.42 g of chloroacetylchloride in 100 ml methylene chloride was added dropwise over 30 minutes and stirred for 1 hour. Water (500 ml) was added, the organic phase separated, washed with water, dried over magnesium sulfate and evaporated under reduced pressure. The resulting residue (27.9 g) in a flask was immersed in a 180° oil bath and the formed benzylchloride removed by distillation. The crude material was chromatrographed on 250 g silica gel using ether for elution. The appropriate fractions were evaporated to dryness and the solid recrystallized from isopropylether to yield 11.0 g 4-benzyl-1-(2-methoxyphenyl)-2-piperazinone in the form of yellowish crystals, mp 109°–111°, pure by TLC (ether on silica gel).

EXAMPLE 23

Preparation of 4-(2-methoxyphenyl)-2-piperazinone hydrochloride

To a solution of 9.4 g of 4-benzyl-1-(2-methoxyphenyl)-2-piperazinone in 100 ml ethanol, 1 g of 5% palladium on carbon was added and hydrogenated at ambient temperature and 15 psi. After 15½ hours, the catalyst was removed by filtration and the filtrate concentrated on a rotary evaporator at 40° to a yellowish liquid (6.8 g) which was dissolved in ethanol saturated with dry hydrochloric acid. After evaporation, the product was crystallized from methanol/ether to give yellowish crystals of 4-(2-methoxyphenyl)-2-piperazinone hydrochloride, mp 209°–211°.

EXAMPLE 24

Preparation of 4-[(1-(3,4-dimethoxybenzyl)-6,7-dimethoxy-4-isoquinoly)methyl]-1-(2-methoxyphenyl)2-piperazinone, 4:5 hydrochloride A solution of 6.4 g of the base 4-(2-methoxyphenyl)-2piperazinone, 100 ml dimethylformamide, 8.4 ml of triethylamine and 11.1 g of 4-chloromethyl-6,7-dimethoxyl-1-[(3,4-dimethoxyphenyl) methyl)] isoquinoline was stirred and heated at 50° for 6 hours. After distillation of the solvent, the residue was mixed with 100 ml of water and extracted 3 times each 150 ml of methylene chloride. The organic layer was washed well with water, dried over magnesium sulfate and evaporated in vacuo to give 18.9 g of a residue which crystallized after trituration with ethanol. After recrystallization from hot ethanol 12.5 g colorless crystals 4-[(1-(3,4-dimethoxybenzyl-6,7-dimethoxy-4-isoquinolyl)methyl]-1-(2-methoxyphenyl)-2-piperazinone, mp 121°–123°, pure by TLC (ethanol on silica gel) were obtained.

$C_{32}H_{35}N_3O_6$ 0,5 $C_2H_5OH$ (580.68) Calculated; C, 68.3; H 6.6; N, 7.2, Found: C, 68.2; H, 6,7; N, 7.4.

The above base on treatment with ethanolic HCl afforded 4-[(1-(3,4-dimethoxybenzyl)-6,7-dimethoxy-4-isoquinoly)methyl]-1-(2-methoxyphenyl)-2-piperazinone hydrochloride, which after recrystallization from ethanol melted at 237°–239° (dec.).

$C_{32}H_{35}N_3O_6$, 1.25 HCl (603.22) Calculated: C, 63.7; H, 6.1; N, 7.0; Cl, 7.3, Found: C, 63.7; H, 6.0, N, 6.9; Cl, 7.2.

EXAMPLE 25

Preparation of tert-butyl-4-(2-methoxyphenyl)-1-piperazinecarboxylate

To a solution of 36.4 g 1-(2-methoxyphenyl)piperazine in 500 ml methylene chloride (anhydrous) was added over 45 minutes under nitrogen with stirring, a solution of 48 g di-tert-butyl dicarbonate in 300 ml methylene chloride (anhydrous). After stirring overnight at room temperature, the solvent was removed under reduced pressure. The yellow residue was dissolved in 300 ml n-hexane and cooled to −20°. After 3 hours the colorless crystals were removed by filtration to give 35.6 of tert-butyl-4-(2-methoxyphenol)-1-piperazine carboxylate, mp 70°–71°.

EXAMPLE 26

Preparation of tert-butyl-4-(2-methoxyphenyl)-1-piperazinecarboxylate4-oxide

To an ice-cooled solution of 35.6 g tert-butyl-4-(2-methoxyphenyl)-1-piperazinecarboxylate in 450 ml methylene chloride was added under nitrogen with stirring over 3½ hours, a solution of 28.8 g m-chloroperbenzoic acid in 450 ml methylene chloride so that the temperature did not exceed 3°–5°. After an additional 3 hours, half of the solvent was removed by distillation and the solution was filtered over 350 g of neutral alumina. After evaporation of the eluent (2000 ml methylene chloride and 1500 ml methylene chloride containing 5% methanol), the residue was crystallized by trituration with isopropylether to give 33.1 g colorless hygroscopic crystals of tert-butyl-4-(o-methoxyphenyl)-1-piperazinecarboxylate 4-oxide, mp 136°–137°.

EXAMPLE 27

Preparation of 1-(2-methoxyphenyl)piperazine 1-oxide

To a stirred ice cold solution of 260 ml trifluoroacetic acid there was added under nitrogen, 26 g of tert-butyl-4-(2-methoxyphenyl-1-piperazinecarboxylate 4-oxide and stirred for another 6 hours at ambient temperature. The solvent was removed in vacuo. The slurry was taken up in 200 ml ether and extracted twice with each 150 ml of water. The aqueous solution was applied to a column packed with 500 g Dowex 2 (x 4, 20-50 mesh, OH−form) and the N-oxide-base eluted with water. After evaporation of the solvent in vacuo, the white foam(18.6 g) was dissolved in a minumum of methylene chloride and the base precipitated by addition of diisopropylether to give 13.1 g colorless hygroscopic crystals of 1-(2-methoxyphenyl)piperazine 1-oxide, mp 157°–160°. The dihydrochloride was crystallized from ethanol/ester, mp 192°–194°.

EXAMPLE 28

Preparation of
1-(3,4-dimethoxybenzyl)-6,7-dimethoxy-4-{-[(4'-(2-methoxyphenyl)-1'-piperazinyl]-methyl}isoquinoline 4'oxide A mixture of 1.72 g of 4-chloro-6,7-dimethoxy-1-[(3,4-dimethoxyphenyl)methyl]isoquinoline, 20 ml dimethyl formamide, 1.3 ml triethylamine and 1.0 g of 1-(2-methoxyphenyl)piperazine 1-oxide was stirred and heated under argon atmosphere at 50° for 4 hours. The cooled solution was poured into ice water, extracted 3 times with methylene chloride and the organic layers washed in turn with water, saturated sodium bicarbonate and water. The combined organic layers were dried over magnesium sulfate and the solvent evaporated in vacuo. The resulting crystalline base was recrystallized from methylene chloride-isopropylether to yield colorless crystals of 1-(3,4-dimethoxyphenyl)6,7-dimethoxy-4-{[4'-(2-methoxyphenyl)-1'-piperazinyl]-methyl} isoquinoline 4'-oxide, mp 205°–206° (dec.), pure by TLC (methanol on silica gel, uv).

$C_{32}H_{37}N_3O_6$ (559.66) Calculated: C,68.7; H, 6.7; N, 7.5 Found: C, 68.4; H, 6.8; N, 7.4.

The trihydrochloride after crystallization from ethanol melted at 203°–210° (dec.):

$C_{32}H_{37}N_3O_6$ 3 HCl, (669.05) Calculated: C, 57.4; H, 6.0; N. 6.3, Found: C, 57.3; H, 6.2; N, 6.3.

EXAMPLE 29

Preparation of
6,7-dimethoxy-4-{[4'-(2-methoyphenyl)-1'-piperazinyl]-methyl} isoquinoline 1',4'-dioxide To an ice-cooled solution of 10.86 g of 6,7-dimethoxy-1-[3,4-dimethoxyphenyl)methyl]-4-[[4-(2-methoxyphenyl)-1-piperazinyl]methyl] isoquinoline in 100 ml methylene chloride under nitrogen was added with stirring a solution of 10.35 g m-chloroperbenzoic acid in 200 ml methylene chloride over 1¾ hours, so that the temperature did not exceed 3°. After 1½ hours, 300 ml methylene chloride were added and the organic phase washed in turn with water, saturated sodium bicarbonate and water, dried over magnesium sulfate and the solvent evaporated in vacuo. The crude yellow crystalline product was recrystallized from methylene chloride isopropyl ether leaving 5.2 g colorless crystals 6,7-dimethoxy-4-{[4'-(2-methoxyphenyl)-1'-piperazinyl]methyl}isoquinoline 1', 4'-dioxide, mp 186°–188° (dec.).

$C_{32}H_{37}N_3O_7$ (575.66) Calculated: C, 67.1; H, 6.6; N, 7.2, Found: C, 66.8; H, 6.5; N. 7.3.

EXAMPLE 30

Preparation of
1-(3,4-dimethoxybenzyl)-6,7-dimethoxy-4{[4'-(2-methoxyphenyl)-1'-piperazinyl]-methyl}isoquinoline 1'oxide To an ice-cooled solution of 33.0 g of 6,7-dimethoxy-1-[-3,4-dimethoxyphenyl)methyl]-4-[[4-(2-methoxyphenyl)-1-piperazinyl]methyl]isoquinoline in 500 ml methylene chloride under nitrogen was added with stirring a solution of 10.4 g m-chloroperbenzoic acid in 200 ml methylene chloride over 3 hours at 0°–3°. The solution was stirred for 20 hours at 0° and applied to a column packed with 700 g silica gel 60 Merck, 230-400 mesh ASTM. Elution with ethyl acetate gave 8.7 g unreacted 6,7-dimethoxy-1-[3,4-dimethoxyphenyl)methyl[-4-[[4-(2-methoxyphenyl)-1-piperazinyl]methyl] isoquinoline. Elution with ethyl acetate/30% ethanol afforded 7.1 g of material which was crystallized from methylene chloride-isopropyl to yield to 5.7 g colorless hygroscopic crystals of 1-(3,4-dimethoxyphenyl)-6,7-dimethoxy-4-{[4'-(2-methoxyphenyl)-1'-piperazinyl]-methyl}isoquinoline 1'-oxide, mp 161°–162°.

$C_{32}H_{37}N_3O_6$ (559.66) Calculated: C, 68.7; H, 6.7; N, 7.5 Found: C, 68.8; H, 7.0; N, 7.3.

Further elution with ethyl acetate/70% ethanol afforded fractions with pure 1-(3,4-dimethoxybenzyl)-6,7-dimethoxy-4-{[4'-(2-methoxybenzyl)-1'-piperazinyl]-methyl} isoquinoline 4'-oxide, mp 204°–206°, from methylene chloride/isopropyl ether (0.9 g).

EXAMPLE 31

Preparation of
4-(chloromethyl)-1-(3,4-dimethoxybenzyl)-6,7-dimethoxyisoquinoline 2-oxide To an ice-cooled solution of 5.2 g 4-chloromethyl-6,7-dimethoxy-1-[(3,4-dimethoxyphenyl) methyl] isoquinoline in 150 ml methylene chloride, was added under stirring and nitrogen a solution of 3.04 g m-chloroperbenzoic acid in 100 ml methylene chloride over 2 hours, so that the temperature did not exceed 3°–5°. The solution was stirred over night at room temperature and the red solution applied to a column, packed with 100 g silica gel 60 Merck, 230-400 mesh ASTM. From elution with ether and ethyl acetate the unreacted base 4-chloromethyl-6,7-dimethoxy-1-[(3,4-dimethoxyphenyl)methyl]isoquinoline was separated. Elution with ethyl acetate/ethanol (4:1) afforded 3.8 g of a brownish foam. The 4-(chloromethyl)-1-(3,4-dimethoxybenzyl)-6,7-dimethoxyisoquinoline 2oxide crystallized from methylene chloride/ethyl acetate: 3.5 g yellow crystals, mp 167°–168°.

EXAMPLE 32

Preparation of
1-(3,4-dimethoxybenzyl)-6,7-dimethoxy-4-{[4'-(2-methoxyphenyl)-1'-piperazinyl]methyl}isoquinoline 2-oxide A mixture of 2.5g 4-chloromethyl-1-(3,4-dimethoxybenzyl-6,7-dimethoxyisoquinoline 2-oxide, 35 ml dimethylformamide, 1.8 triethylamine and 1.29 g 1-(2-methoxyphenyl)piperazine was stirred and heated under nitrogen at 50° for 7 hours. After evaporation of the solvent, the residue was partitioned between methylene chloride and water. The methylene chloride solution was washed with water and dried. After removal of the solvent in vacuo, the residue (3.5 g) was crystallized from methylene chloride/ethyl acetate to yield 3.05 g of yellow, hygroscopic crystals of 1-(3,4)-dimethoxybenzyl)-6,7-dimethoxy-4-{]4'-(2-methoxyphenyl)-1'-piperazinyl]methyl} isoquinoline 2-oxide, mp 128°–129° (dec.).

$C_{32}H_{37}N_3O_6$ (559.66) Calculated: C, 68.7; H, 6.7; N, 7.5 Found: C, 68.7; H, 6.9; N, 7.4.

The dihydrochloride after crystallization from ethanol/ether melted at 202°–204° (dec.).

$C_{32}H_{37}N_3O_6$ 2 HCl (632.59) Calculated: C, 60.8; H, 6.1; N, 6.7; Cl, 11.4, Found: C, 61.1; H, 6.1; N, 6.7; Cl. 11.4.

EXAMPLE 33

Preparation of 1-(3,4-dimethoxybenzyl)-6,7-dimethoxy-4-{[4'-(2-methoxyphenyl)-1"-piperazinyl]methyl}isoquinoline 2,4'-dioxide A mixture of 582 mg 4-chloromethyl-1-(3,4-dimethoxybenzyl)-6,7-dimethoxyisoquinoline 2-oxide, 10 ml dimethyformamide, 0.4 ml triethylamine and 0.3 g 1-(2-methoxyphenyl) piperazine 1-oxide was treated as described for the preparation of 1-(3,4-dimethoxybenzyl)-6,7-dimethoxy-4-{[-(2-methoxyphenyl)-1'-piperazinyl]methyl} isoquinoline 2-oxide. After evaporation of the solvent the residue was chromatographed on 10 g silica gel. Elution with ethyl acetate/ethanol (2.3) yielded 180 mg of a brownish foam which crystallized from ethyl acetate/ether to yield 1-(3,4-dimethoxybenzyl)-6,7-dimethoxy-4-{[4'-(2-methoxyphenyl)-1"-piperazinyl]methyl} isoquinoline 2,4'-dioxide, mp 161°–163°, different from 6,7-dimethoxy-4-{[4'-(2-methoxyphenyl)-1'-piperazinyl]methyl}isoquinoline 1', 4'-dioxide by TLC (methanol on silica gel, uv).

$C_{32}H_{37}N_3O_7$ (575.66). Calculated: C, 66.8; H, 6.5; N, 7.3 Found: C, 66.5; H, 6.5; N, 7.1.

EXAMPLE 34

Preparation of 6,7-dimethoxy-1-[(3,4-dimethoxyphenyl)methyl]-4-isoquinoline methanol A slurry of 25.2 g of 6,7-dimethoxy-1-[(3,4-dimethoxyphenyl)methyl]-4-isoquinolinecarboxylic acid and 100 of dry tetrahydrofuran was stirred at 15° in an inert atmosphere while cautiously adding 200 ml of 1 molar borane/tetrahydrofuran complex. After stirring for 2 hours at room temperature, the initial solids had dissolved and were replaced by a second precipitate. The mixture was cautiously treated with 200 ml of water and the tetrahydrofuran was removed in vacuo at 40°. The chilled reaction mixture was then filtered, washed with water, and the damp stable borane complex was added portionwise with stirring to 200 ml of 2 N hydrochloric acid previously heated to 70°–80°. The resulting solution was heated an additional 15 minutes on the steam bath and was then chilled extracted with 100 ml of diethyl ether. The aqueous layer was added dropwise to 250 ml of cold 2 N sodium hydroxide with stirring. The resulting solids were removed by filtration, washed well with water, and dried to give 20.6 g of crude 6,7-dimethoxy-1[(3,4-dimethoxyphenyl)methyl]-4-isoquinoline methanol, mp 146°–148°. Recrystallization from methylene chloride/ethyl acetate gave 19.2 g of purified 6,7-dimethoxy-1-(3,4-dimethoxyphenyl)methyl]-4-isoquinoline methanol, mp 141°–143°.

EXAMPLE 35

TABLET FORMULATIONS
(Direct Compression)

| Item | Ingredients | mg/tablet | mg/tablet | mg/tablet |
|---|---|---|---|---|
| 1. | 6,7-dimethoxy-1-[(3,4-dimethoxyphenyl)methyl]-4-[[4-(2-methoxyphenyl)-1-piperazinyl]methyl]isoquinoline | 15 | 30 | 60 |
| 2. | Lactose | 207 | 192 | 162 |
| 3. | Avicel | 45 | 45 | 45 |
| 4. | Direct Compression Starch | 30 | 30 | 30 |
| 5. | Magnesium Stearate | 3 | 3 | 3 |
|  | Weight of tablet | 300 mg | 300 mg | 300 mg |

Procedure:
(1) Mix Item 1 with an equal amount of lactose. Mix well.
(2) Mix with Items 3,4 and remaining lactose. Mix well.
(3) Add the magnesium stearate and mix for 3 minutes.
(4) Compress on a suitable punch.

EXAMPLE 36

TABLET FORMULATIONS
(Wet Granulation)

| Item | Ingredients | mg/tablet | mg/tablet | mg/tablet |
|---|---|---|---|---|
| 1. | 6,7-dimethoxy-1-[(3,4-dimethoxyphenyl)methyl]-4-[[4-(2-methoxyphenyl)-1-piperazinyl]methyl]isoquinoline | 50 | 100 | 200 |
| 2. | Lactose | 153 | 187 | 171 |
| 3. | Modified starch | 25 | 35 | 45 |
| 4. | Pregelatinized starch | 20 | 25 | 30 |
| 5. | Distilled water q.s. | — | — | — |
| 6. | Magnesiun stearate | 2 | 3 | 4 |
|  | Weight of tablet | 250 mg | 350 mg | 450 mg |

Procedure:
(1) Mix Items 1–4 in a suitable mixer.
(2) Granulate with sufficient distilled water to proper consistency. Mill.
(3) Dry in a suitable oven.
(4) Mill and mix with magnesium stearate for 3 minutes.
(5) Compress on a suitable press equipped with appropriate punches.

EXAMPLE 37

CAPSULE FORMULATIONS

| Item | Ingredients | mg/capsule | mg/capsule | mg/capsule |
|---|---|---|---|---|
| 1. | 6,7-dimethoxy-1-[(3,4-dimethoxyphenyl)methyl]-4-[[4-(2-methoxyphenyl)-1-piperazinyl]methyl]isoquinoline | 50 | 100 | 200 |
| 2. | Lactose | 155 | 200 | 140 |
| 3. | Starch | 30 | 35 | 40 |
| 4. | Talc | 15 | 15 | 20 |
|  | Capsule fill weight | 250 mg | 350 mg | 400 mg |

Procedure:
(1) Mix Items 1–3 in a suitable mixer. Mill.
(2) Add talc and mix well.
(3) Encapsulate on suitable equipment.

EXAMPLE 38

CAPSULE FORMULATIONS

| Item | Ingredients | mg/capsule | mg/capsule | mg/capsule |
|---|---|---|---|---|
| 1. | 6,7-dimethoxy-1-[(3,4-dimethoxyphenyl)methyl]-4-[[4-(2-methoxyphenyl)-1-piperazinyl]methyl]isoquinoline | 15 | 30 | 60 |
| 2. | Lactose | 239 | 224 | 194 |

-continued

CAPSULE FORMULATIONS

| Item | Ingredients | mg/capsule | mg/capsule | mg/capsule |
|---|---|---|---|---|
| 3. | Starch | 30 | 30 | 30 |
| 4. | Talc | 15 | 15 | 15 |
| 5. | Magnesium Stearate | 1 | 1 | 1 |
|  | Capsule fill weight | 300 mg | 300 mg | 300 mg |

Procedure:
(1) Mix items 1–3 in a suitable mixer.
(2) Add talc and magnesium stearate and mix for a short period of time.
(3) Encapsulate on an appropriate encapsulation machine.

EXAMPLE 39

TABLET FORMULATIONS
(Wet Granulation)

| Item | Ingredients | mg/tablet | mg/tablet | mg/tablet |
|---|---|---|---|---|
| 1. | 6,7-dimethoxy-1-[(3,4-dimethoxyphenyl)methyl]-4-[[4-(2-methoxyphenyl)-1-piperazinyl]methyl]isoquinoline | 15 | 30 | 60 |
| 2. | Lactose | 188 | 173 | 188 |
| 3. | Modified starch | 25 | 25 | 30 |
| 4. | Pregelatinized starch | 20 | 20 | 20 |
| 5. | Distilled water q.s. | — | — | — |
| 6. | Magnesium stearate | 2 | 2 | 2 |
|  | Weight of tablet | 250 mg | 250 mg | 300 mg |

Procedure:
(1) Mix Items 1–4 in a suitable mixer.
(2) Granulate with sufficient distilled water to proper consistency. Mill.
(3) Dry in a suitable oven.
(4) Mill and mix with magnesium stearate.
(5) Compress on a suitable press for 3 minutes equipped with appropriate punches.

We claim:

1. A compound of the formula

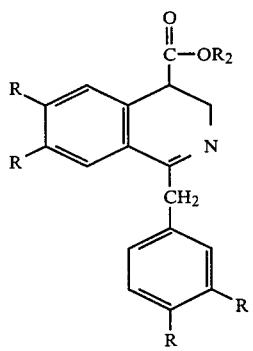

wherein R is lower alkoxy, and $R_2$ is hydrogen or lower alkyl.

2. A compound in accordance with claim 1, which is 3,4-dihydro-6,7-dimethoxy-1-[(3,4-dimethoxyphenyl)methyl]-4-isoquinoline carboxylic acid.

3. A compound in accordance with claim 1, which is 3,4-dihydro-6,7-dimethoxy-1-[(3,4-dimethoxyphenyl)methyl]-4-isoquinoline carboxylic acid ethyl ester.

4. A compound of the formula

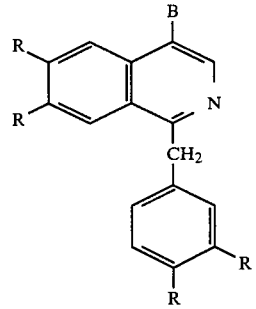

wherein R is lower alkoxy, and B is hydroxymethyl or

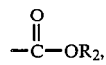

wherein $R_2$ is hydrogen or lower alkyl.

5. A compound in accordance with claim 4, which is 6,7-dimethoxy-1-[(3,4-dimethoxyphenyl)methyl]-4-isoquinolinecarboxylic acid.

6. A compound in accordance with claim 4, which is 6,7-dimethoxy-1-[(3,4-dimethoxyphenyl)methyl]-4-isoquinoline methanol.

7. A compound of the formula

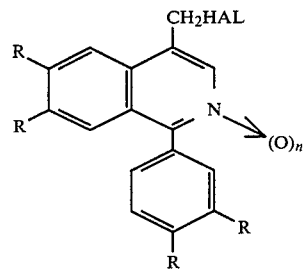

wherein R is lower alkoxy, n is the integer zero or 1, and HAL is halogen.

8. A compound in accordance with claim 7, which is 4-chloromethyl-6,7-dimethoxy-1-[(3,4-dimethoxyphenyl)methyl]isoquinoline.

* * * * *